United States Patent [19]

Boeckel

[11] 4,327,661
[45] May 4, 1982

[54] CHAMBER BLOCK HAVING A SUPERNATANT COLLECTION RECEPTACLE THEREIN

[75] Inventor: John W. Boeckel, Hamden, Conn.

[73] Assignee: E. I. Du Pont de Nemours and Company, Wilmington, Del.

[21] Appl. No.: 175,501

[22] Filed: Aug. 5, 1980

[51] Int. Cl.³ .................. B05C 13/02; B04B 11/00
[52] U.S. Cl. .................. 118/52; 233/1 R; 427/240; 427/2; 118/407
[58] Field of Search .................. 233/13, 26, 27, 28, 233/34, 38, 45, 46, 1 R; 118/52, 407; 427/2, 240

[56] References Cited

U.S. PATENT DOCUMENTS

| 3,352,280 | 11/1967 | Hughes | 118/319 |
| 3,619,865 | 11/1971 | Hazzard | 118/52 |
| 3,705,048 | 12/1972 | Staunton | 427/2 |
| 3,906,890 | 9/1975 | Amos | 427/2 |
| 4,093,350 | 6/1978 | Fisli | 118/52 |

Primary Examiner—Robert W. Jenkins

[57] ABSTRACT

A chamber block removably insertable into a centrifuge rotor of the type used for the preparation of cell dispersions on slides is characterized by a opening formed in the chamber block which, when closed, defines a supernatant collection receptacle within the block. A deflection baffle is disposed within the chamber block so that supernatant withdrawn through a suction conduit from the vicinity of the slide is deflected into the collection receptacle.

10 Claims, 7 Drawing Figures

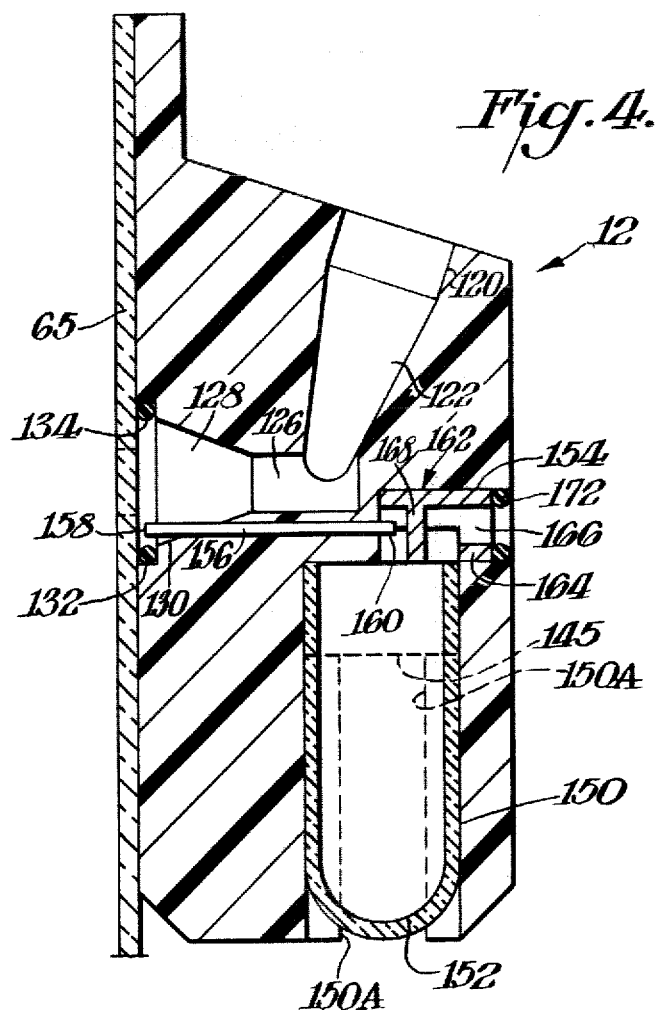

CHAMBER BLOCK HAVING A SUPERNATANT COLLECTION RECEPTACLE THEREIN

FIELD OF THE INVENTION

This invention relates to a centrifuge rotor of the type adapted to deposit particles suspended within a supernatant onto a deposition surface and, in particular, to a chamber block having a deflection baffle therein adapted to direct supernatant into a supernatant collection receptacle formed within the chamber block.

CROSS-REFERENCE TO RELATED APPLICATION

Subject matter disclosed herein is disclosed and claimed in copending application Ser. No. 175,500, filed in the name of Robert Joseph Bouclier on Aug. 5, 1980.

BACKGROUND ART

Samples of bodily fluids, such as blood and the like, derived from patients usually include particulate matter suspended in a liquid medium known as a supernatant. The suspended particulate matter may, for example, include cellular material, cells, and bacteria. When it is desired to closely analyze such particulate matter (hereafter "particles") it is usually necessary to deposit those particles upon suitable deposition surfaces, as microscope slides, so that further examination may occur. The deposition of the particles on the slide is usually accomplished through the use of a centrifuge apparatus. Rotation of the centrifuge rotor causes the particles to move under the influence of a centrifugal force field and impact, or sediment, upon the slide. The supernatant is also impelled by the force field toward the slide. However, the supernatant must be removed so that the sedimented cells can remain in position on the slide.

Devices such as that available from Shandon-Elliot and sold under the name "Cytospin" have been used to concentrate particles on slides. In this device, filter paper has been used to withdraw excess supernatant from the surface of the slide. It has been observed, however, that the use of filter paper for such a purpose has the tendency to absorb or to draw cells from the slide's surface. This is perceived as disadvantageous.

The problems attendant with the use of filter paper as the supernatant absorbing medium are believed to be overcome by a device described and claimed in copending application Ser. No. 15,911, filed Feb. 28, 1979 and in copending application Ser. No. 131,678, filed Mar. 19, 1980, both assigned to the assignee of the instant invention. Such a device, which is manufactured and sold by Sorvall Division of E. I. du Pont de Nemours and Company utilizes removable chamber blocks each of which includes an inlet channel into which a sample suspension is introduced and an outlet channel through which the supernatant and particles travel under the influence of a centrifugal force toward the slide surface. A conduit is formed within the chamber block with one end of the conduit being disposed in the vicinity of the outlet orifice and the surface of the slide. The other end of the conduit is communicable with an external suction device. When a suction is applied to the conduit excess supernatant is withdrawn from the surface of the slide, thus permitting the sedimented cells to remain in position on the slide surface.

Since in some instances the amount of the sample is limited, it is believed desirable to provide an arrangement whereby the supernatant may be withdrawn without commingling that supernatant with supernatant used to support particles from other samples. Thus, that portion of the specimen particles not deposited on the slide may advantageously be individually retrieved and held for further use. It is also believed desirable to provide a centrifuge rotor arrangement whereby samples, which may be radioactively tagged or otherwise treated, may be sedimented and the supernatant which supports such particles segregated. Such an arrangement would isolate the supernatant which supported the treated particles, thus avoiding contamination of common external collection bottles or of the centrifuge.

DISCLOSURE OF THE INVENTION

This invention relates to a centrifuge rotor having removable chamber blocks mountable therein, each chamber block being provided with an inlet channel for introducing a sample containing a supernatant having particles suspended therein and an outlet channel through which the particles and supernatant are moved under the influence of centrifugal force onto a deposition surface. The first end of a supernatant withdrawal conduit is disposed in the vicinity of the outlet channel adjacent to the slide surface. The second end of the conduit is communicable with an opening formed in the chamber block. The opening is closable by a suitable closure member, as a plug or a strip of tape. When closed, an enclosed supernatant collection receptacle is formed in the block. An aperture formed in the block is communicable with an external suction device and with the receptacle to produce a lower pressure region in a portion of the receptacle. A deflection baffle is mounted in a recess provided in the block and positioned with respect to the second end of the conduit such that supernatant withdrawn through the conduit toward the lower pressure region is deflected by the baffle into the supernatant collection receptacle.

BRIEF DESCRIPTION OF THE DRAWINGS

The invention will be more fully understood from the following detailed description thereof, taken in connection with the accompanying drawings, which form a part of this application and in which:

FIG. 4 is a side elevation view, entirely in section, of a chamber block in accordance with the preferred embodiment of the invention;

FIG. 5 is a bottom view of the chamber block shown in FIG. 4;

DETAILED DESCRIPTION OF THE INVENTION

Figure 1:
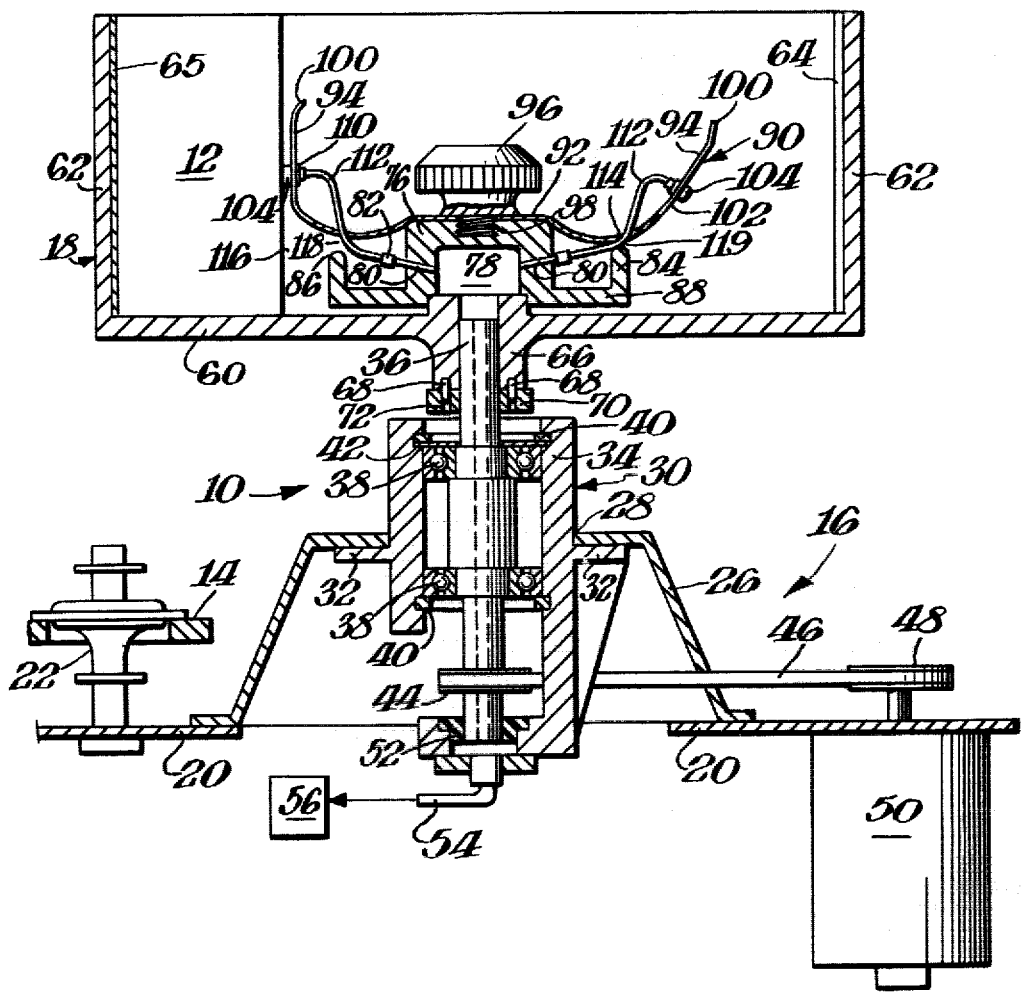
FIG. 1 is a partial section view of a bowl-type centrifuge rotor in which a chamber block in accordance with this invention may be disposed.

Throughout the following description similar reference numerals refer to similar elements in all figures of the drawings.

There may be seen in FIG. 1 a cross section illustration of a centrifuge, generally indicated by reference numeral 10, with which a chamber block in accordance with this invention and generally indicated by reference numeral 12 may be used. It is understood that the particular details of the outer housing for the centrifuge 10 are not shown since it is not an inherent part of the invention. Any suitble housing, such as is typically used for a cell washer or small laboratory type centrifuge, may be used. It is noted that the housing should preferably contain an aspiration system. The centrifuge 10 described in FIGS. 1-3 generally corresponds to the device disclosed and claimed in the copending application of Boeckel et al., Ser. No. 131,678, filed Mar. 19, 1980. However, it is to be understood that a chamber block 12 in accordance with this invention may be utilized in a centrifuge such as disclosed and claimed in the copending application of Boeckel et al., Ser. No. 15,911, filed Feb. 28, 1979, or with any other suitably arranged centrifuge.

The centrifuge 10 includes a chassis 14 to which a rotor drive assembly 16 and a centrifuge rotor 18 are secured. Thus a mounting plate 20 for the centrifuge rotor drive assembly 16 is resiliently secured to the chassis 14 as by a conventional vibration mount 22 formed of a resilient material. This serves to isolate the mounting plate 20 from the chassis 14 so that mechanical vibrations are not transmitted to the chassis. A mounting cone 26 may be secured, as by welding, to the mounting plate 20. The mounting cone 26 has a central opening 28 in which is secured a drive cartridge assembly 30. The drive cartridge assembly 30 has a flange 32 and is secured to the mounting cone 26 by any suitable means. For example, the flange 32 may be welded to the underside of the cone 26 adjacent the opening 28 therein.

The drive cartridge assembly 30 includes an outer sleeve 34 in which is secured a hollow drive shaft 36. The drive shaft is mounted within the sleeve 34, as by bearings 38. The bearings 38 are secured in position by a C-ring 40 and a wavy washer 42. The exterior of the hollow shaft 36 is undercut to facilitate its mounting within the bearings and to prevent axial movement of the shaft. The lower portion of the shaft has a drive pulley 44 secured thereto and is driven by means of a belt 46 which in turn is driven by the drive pulley 48 of a motor 50. The motor 50 may be mounted to the mounting plate 20. The extreme lower end portion of the hollow drive shaft 36 is rotated within a stationary seal 52 to which is attached a vacuum takeoff line 54. The takeoff line is in turn coupled to a vacuum source, as a vacuum pump, shown diagrammatically at 56. Suitable for use as the pump 56 is a device manufactured and sold by New Venture Technology Corporation under model number V3.

Figure 2:
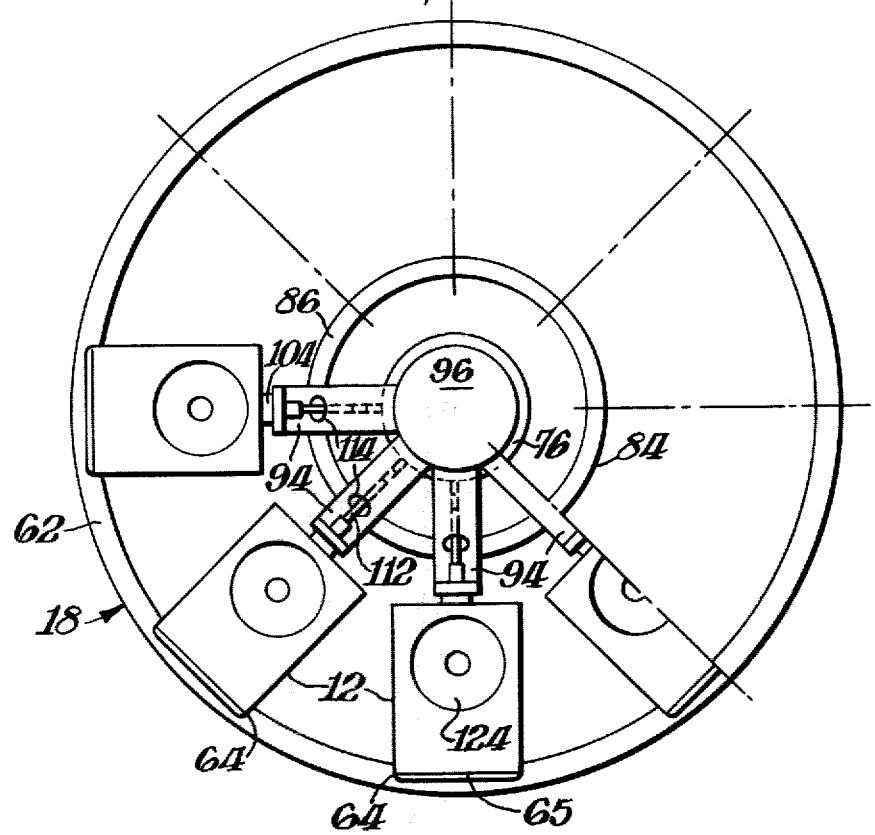
FIG. 2 is a plan view of a centrifuge rotor of FIG. 1.
Figure 3:
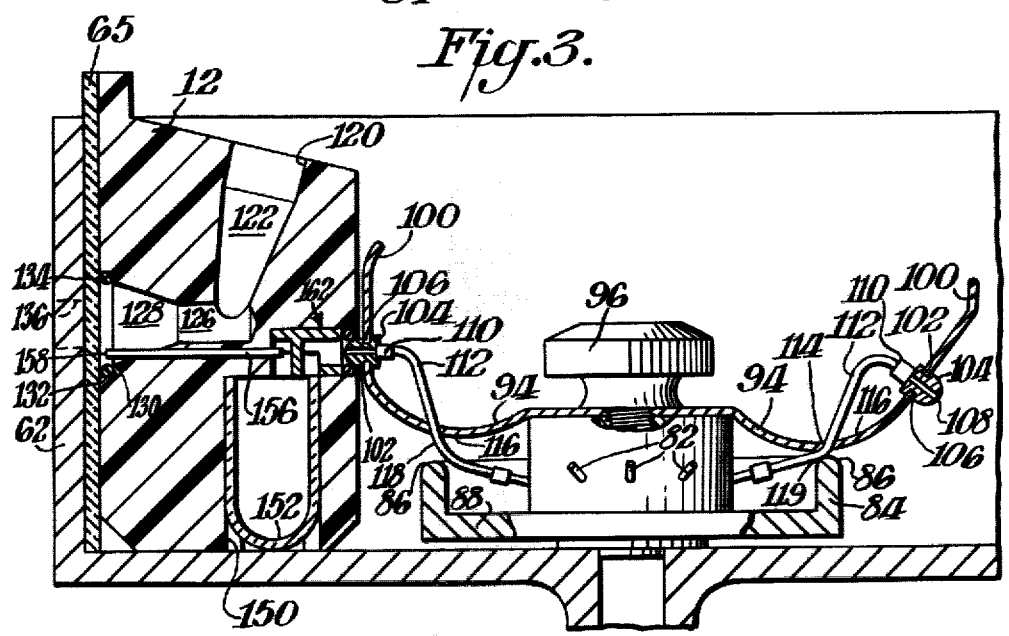
FIG. 3 is an elevation view entirely in cross section illustrating the chamber block as received by the rotor of FIG. 1.
Figure 6:
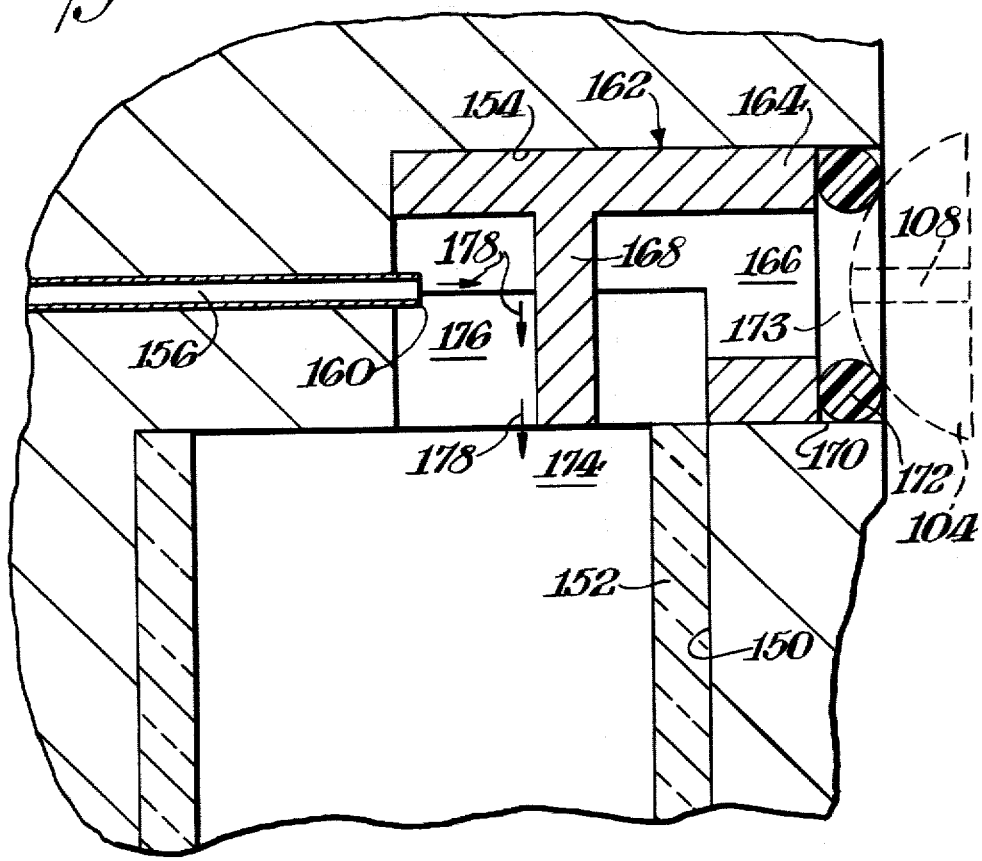
FIG. 6 is an enlarged view of the operation of the deflection baffle.
Figure 7:
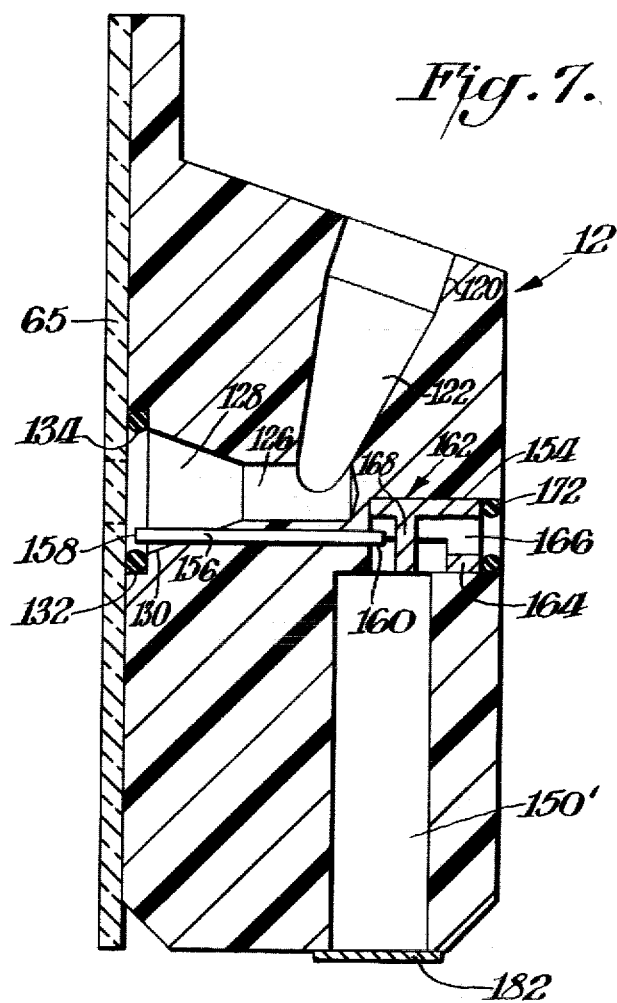
FIG. 7 is a side elevation view, entirely in section, of an alternative embodiment of a chamber block in accordance with the invention.

The rotor 18 is removably mounted on the top end of the drive shaft 26. This is accomplished by forming the rotor 18 so that it exhibits a bowl-like configuration with a base 60 and side wall 62. The inner portion of the side wall 62 is provided with vertically oriented, peripherally spaced slots 64. The slots 64 are adapted to define regions each sized to accommodate and support an individual chamber block 12 and a deposition surface 65, such as a microscope slide. An individual chamber block 12 in accordance with the preferred embodiment of the instant invention is shown in FIGS. 4-6. An alternate embodiment of a chamber block is shown in FIG. 7. The manner in which individual blocks 12 are received within the rotor 18 is illustrated in FIGS. 1-3, but is believed best illustrated in FIG. 3.

A hub 66 is formed in the central portion of the base 60 of the rotor 18 and is provided with two pins 68 mounted thereon. The hub 66 is placed over the upper end of the hollow drive shaft 36 and rests upon a shaft mounting collar 70 having holes 72 formed therein. The holes 72 are located to engage the pins 68 to form a secure interconnection between the rotor 18 and the drive assembly 16 therefor.

A collection cap 76 is secured by a friction fit or other suitable means (to afford a quick disconnect for cleaning) to the hub 66 on the base 60 of the rotor 18. The collection cap 76 cooperates with the hub 66 to provide a central vacuum cavity 78 which communicates with the hollow drive shaft 36. In this manner, vacuum may be applied from the pump 56 through the drive shaft 36 to the cavity 78. Orifices 80 are formed peripherally through the collection cap 76 and define a slightly upward orientation as they extend outwardly from the cavity 78. The orifices 80 are each provided with a connection nipple 82. An annular ring 84 having an upper clamping surface 86 thereon is supported by a web 88 from the lower portion of the collection cap 76 for a purpose set forth herein.

A nozzle support element, generally indicated by reference character 90, includes a flat central body portion 92 from which an array of resilient leaf spring arms 94 extend. The nozzle support element 90 may be secured to the cap 76 in any convenient manner, as by the threading of a clamping knob 96 into a threaded recess 98 provided in the cap 76 for that purpose. The leaf spring arms 94 extend radially outwardly from the cap 76 toward the chamber-receiving regions at the periphery of the rotor, with one arm 94 being allocated to service each of the chamber blocks 12 which may be inserted into and received by the regions in the rotor. The outward one of each arm 94 is bent, as at 100, to facilitate manipulation of the arm 94 to permit the block 12 with which it is associated to be inserted into the rotor. Located near the outward end of each arm 94 is a hole 102 into which a nozzle member 104 may be received. The nozzle 104 has an annular slot 106 therein, which acts in the nature of a grommet, to engage the edges of the hole 102 so that the nozzle 104 my be properly mounted to its associated leaf spring arm 94.

A channel 108 (FIG. 3) extends through the nozzle 104 and terminates into a rearwardly extending nipple 110. A flexible connection tube 112 interconnects the nipple 110 at the rear of the nozzle 104 to the connection nipples 82 on the cap 76. The tube 112 passes through an opening 114 provided in the bent elbow region 116 of each arm 94. Thus, as the tubing 112 extends inwardly toward the cap, the tubing passes through the hole 114 beneath the arm 94. As is shown in FIGS. 1 and 3, when a chamber block 12 is recieved within the region associated with a given arm, (as in the left-hand side of FIGS. 1 and 3), the engagement of that arm 94 and the block 12 causes the arm to retract so that a vertical clearance 118 is defined between the clamping surface 86 of the ring 84 and the lower surface of the arm 94. Thus, free communication is permitted through the tubing 112 between the nozzle 104 and the cavity 78 in the cap. Conversely, when an arm 94 is not retracted by association with a chamber block, the resilient spring force of the arm urges that arm downwardly to constrict the tube 112 between the underside of the arm and the clamping surface 86 of the ring 84, illustrated by reference character 119 (FIGS. 1 and 3). During centrifugation, the arm 94 moves outwardly further constricting the tube 112 against the clamping surface 86 of the ring 84.

Reference is invited to FIGS. 4 and 5, which respectively disclose a cross section and bottom view of an individual one of the chamber blocks 12 in accordance with the preferred embodiment of the instant invention. Each of the individual chamber blocks 12 is a member preferably rubbermolded from a clear epoxy material. Each block 12 includes an inlet orifice 120 communicating with an inlet channel 122. The inlet channel 122 is inclined at about 20° with the vertical to preclude supernatant or particles from being centrifuged from the block 12. The block 12 may be provided with a cover 124 (FIG. 2) if desired. The lower end of the inlet channel 122 communicates through a transition region 126 to a diverging outlet channel 128 terminating in an outlet orifice 130. The chamber block 12 is provided with a notch 132 in the vicinity of the outlet orifice 130 to permit the block 12 to receive a suitable quad-ring gasket 134. Such quad-ring gaskets are preferred at the interface of the block 12 and the deposition surface, or slide, 65 since they minimize capillary action which may draw particles onto the slide. The gaskets 134 are those manufactured of a fluoroelastomer material such as that sold by E. I. du Pont de Nemours and Company under the trademark VITON. A suitable gasket 134 is sold by Minnesota Rubber Co., Minneapolis, Minn. under part number 4012. The gasket 134, when the chamber block 12 is placed within the rotor (as in FIG. 3) contacts the deposition surface 65 and thus defines a sealed region on the deposition surface 65 onto which the particles carried in the supernatant may be deposited. If desired, the region of the deposition surface 65 bounded by the gasket 134 may be visually inspected from the exterior of the rotor through the viewing ports 136 which may be provided for that purpose.

As best seen in the bottom view of chamber block shown in FIG. 5, the chamber block 12 is formed in a stepped configuration, with four distinct width dimensions being defined, as illustrated at 142A, 142B, 142C and 142D. A portion of the block 12 exhibiting the dimension 142C is cut away along a surface 145 (FIG. 4, approximately midway of the height of the block 12) to the lower end of the block 12 to define the narrower portion 142C seen in the bottom view (FIG. 5). The widest dimension 142D forms arms 144 which are notched, as at 146. The notches 146 define a trackway which receives the deposition surface 65 and prevents its movement with respect to the block 12. When the block 12 is inserted into the rotor 18, the dimension 142D lies next radially adjacent to the inside surface of the outer wall 62. When the block 12 is inserted, both the force of the spring arm 94 and centrifugal force urge the block 12 into tight engagement with the deposition surface. A clearance distance 148 is defined between the surface of the arms 144 and the inside of the rotor wall 62 to insure that the block may move radially outwardly to firmly engage the deposition surface 65.

Each of the chamber blocks 12 is provided with an opening 150 extending substantially vertically through a portion thereof. In the preferred embodiment, the opening 150 is sized to closely receive and frictionally support a removable supernatant collection vial 152. When the vial 152 is inserted into and received by the opening 150, an enclosed supernatant collection receptacle is defined within the block 12. As is discussed hereafter in connection with FIG. 7, alternate means may be utilized to define the enclosed supernatant collection receptacle in accordance with the instant invention.

The opening 150 is provided in that portion of the block 12 which exhibits the width dimension 142B and extends into the portion of the block 12 above the surface 145 which exhibits the dimension 142C. The opening 150 is itself of a greater width dimension than the portion of the block having the dimension 142B to define cut-out portions 150A and 150B so that when the vial 152 is received within the opening 150, lateral surfaces 152A and 152B on the vial 152 protrude beyond the dimension of the block 12. This facilitates insertion and withdrawal of the vial 152 from the block 12. It is noted that the opening 150 is machined to within a predetermined close tolerance of the dimension of the vial 152, so that when the vial 152 is received within the opening 150 in a close fitting relationship therewith the provision of a separate seal is not necessary to maintain sealed intergrity between the outer surface of the vial 152 and the boundary of the opening 150. When inserted into the opening 150, the upper end of the vial 152 seats within the portion of the block above the surface 145, so that the full circumference of the vial is recieved by and abuts against the material of the block 12.

Communicating with the uppermost portion of the opening 150 is a counterbored recess 154. The axis of the counterbored recess 154 is shown in FIGS. 3-6 as extending substantially perpendicularly to the axis of the opening 150. However, it is to be understood that any suitable size, configuration and location of the recess 154 with respect to the opening 150 may be utilized to effect the purposes of the instant invention as set forth herein.

A supernatant withdrawal conduit or canulla 156 is provided within the body of the chamber block 12. The radially outer end 158 (FIG. 3) of the conduit 156 is disposed in the vicinity of the outlet orifice 130 and lies within a predetermined close distance of the deposition surface 65. The end 158 of the conduit 156 lies within the region bounded by the gasket 134. When a wet slide is used, the end 158 of the conduit 156 lies within about ten-thousandths of an inch of the slide. When using a dry slide, the conduit 156 may actually touch the slide, with the serrations at the end of the conduit (formed when the conduit is cut) defining inlets through which the supernatant may enter the conduit.

The inner end 160 of the conduit 156 farthest (the end from the end 158) communicates with the opening 150. In the Figures, the end 160 protrudes into the counterbored recess 154, although any arrangement suitable to effect the purposes set forth herein may be used.

A deflection member, or inset, 162 is insertable into the counterbored recess 54. The member 162 is substantially cylindrical and elongated in configuration and includes an annular collar portion 164 having an aperture 166 therethrough and a solid (non-apertured) plate portion 168 axially spaced from the collar 164. When inserted into and received by the recess 154 in the block 12, the plate portion 168 is proximal to the inner end 160 of the conduit 156. Also, when inserted into and received by the recess 154, the end of the member 162 is set back from the edge of the recess 154 to define a notch 170 which receives an O-ring seal 172. The opening 173 in the seal 172 registers and communicates with the aperture 166 in the collar 169. The seal 172 may be made of a material similar to the material used for the gasket 134. When the member 162 and the O-ring 172 are inserted into the recess 154, the O-ring 172 forms a landing which receives the nozzle 104. The recess 154 and the opening 150 may communicate through the aperture 166 with the external suction device through this interconnection with the nozzle 104. The plate 168 across the recess 154 interrupts "line of sight" passage between the inner end 160 of the conduit 156 and the aperture 166. The deflection member 162 may be molded or machined of any suitable material, although a polycarbonate material such as sold under the trademark LEXAN by General Electric Company is preferred.

In operation, a deposition surface 65 is mounted into the trackway on the chamber block 12 with which it is associated. The chamber block 12 and deposition surface 65 are vertically inserted into one of the regions in the rotor by retracting the arm 94 in a radially inward direction. After insertion of the block 12, the arm 92 is released so that the bias of the spring urges the nozzle 96 into the landing area defined by the O-ring gasket 172. The force of the arm 94 also urges the block 12 outwardly to compress the block against the deposition surface 65. It is desirable that chamber blocks 12 be inserted into diametrically opposed regions of the rotor to prevent rotor unbalance during operation. Of course, if only one chamber block is utilized, a suitable counterbalance should be provided diametrically from that block.

A sample of suspended particles and supernatant is introduced into the inlet channel 122 through the inlet orifice 120. The centrifuge is operated at the appropriate rotational speed so that the particles and supernatant move under the influence of the centrifugal force field through the transition region 126, through the outlet channel 128 and the outlet orifice 130. The particles are sedimented or deposited upon that portion of the surface 65 bounded by the gasket 134.

When centrifugation is completed, the suction device 56 may be energized, and a suction applied through the interconnection with the individual blocks 12 (through the hollow shaft 36, the cavity 78, the tubing 112, the channel 108 in the nozzle 104 and the aperture 166). The suction evacuates the region 174 below the plate 168 and in the upper portion of the vial 152 and the region 176 between the plate 168 and the inner end 160 of the conduit. The suction also extends through the conduit 156 to the vicinity of the deposition surface.

As the supernatant is withdrawn through the conduit 156 toward the lower pressure region 174 in the upper portion of the opening, the downwardly depending plate portion 168 physically interdicts the flow of supernatant being withdrawn through the action of the suction. The supernatant is deflected into the collection vial 152. It is noted that the presence of lower pressure region 174 above the vial 152 assists in drawing the deflected supernatant into the vial 152. The deflection action afforded by the plate 168 is illustrated in FIG. 6 by arrows 178.

The suction may be removed and each of the chamber blocks 12 withdrawn. The individual collection vials 152 may then be removed and the supernatant retained for further use or discarded.

As may be appreciated from the foregoing, when the vial 152 is received within the opening 150, the vial 152 cooperates with the block 12 to define an enclosed supernatant collection receptacle within the block 12. However, the enclosed supernatant collection receptacle may be defined in other ways, which should be understood as falling within the contemplation of the instant invention.

With respect to FIG. 7, an alternate embodiment of the invention is shown in which an opening 150' is disposed within the block 12 so that a portion of the opening 150' communicates with the end 160 of the conduit 156 and with the deflection plate 168 of the member 162. The opening 150' may be any predetermined width dimension so long as the opening is bounded by material of the block. The axis of the opening 150' may exhibit any orientation with respect to the axis of the recess 154.

The opening 150' is closable by any suitable closure member 182, shown in FIG. 7 as a strip of adhesive tape, which may be releasably disposed or removably mountable across the mouth of the opening. The closure member 182, when disposed across the mouth of the opening 150', encloses and seals the opening 150' to define the enclosed supernatant collection receptacle within the block 12. With the closure member 182 in place, the suction may effectively evacuate the regions 174 and 176 and the conduit 156, thus withdrawing supernatant from the region of the deposition surface in the manner discussed above. The baffle plate 168, in the manner discussed earlier, deflects the withdrawn supernatant into the enclosed receptacle where it is collected. Thereafter, the closure member 182 may be removed to drain the collected supernatant from the receptacle.

Of course, other suitable arrangements may be utilized to close the opening 150' and thus define the enclosed supernatant collection receptacle. For example, the closure member may take the form of a cap which may be inserted into the mouth of the opening 150' and thus provide the sealed, enclosed receptacle. Alternatively, the closure member may be in the form of a plug member which is received by the opening 150'. Any other alternatives whereby the opening 150' may be enclosed to define the collection receptacle and thereafter opened to drain the supernatant collected therein may also be utilized to effect the purposes above set forth.

It should be appreciated from the foregoing that there has been described a centrifuge rotor and a chamber block for use therein which permits individual collection and segregation of supernatant withdrawn from the vicinity of the deposition surface. The deflection baffle, depending into the lower pressure region produced in the upper portion of the opening, interdicts the flow of supernatant withdrawn through the conduit into the vial.

Those skilled in the art, having the benefit of the teachings herein set forth may effect modifications to the embodiment of the invention described. However, it is to be understood that such modifications lie within the scope of this invention, as defined by the appended claims.

What is claimed is:

1. In a chamber block adapted for removable insertion into and out of a centrifuge rotor, the chamber block being of the type having
    (a) a channel through which particles and a supernatant in which they are suspended move under the influence of centrifugal force toward a deposition surface, and
    (b) a conduit through which supernatant is withdrawn by suction from the region of the deposition surface;

wherein the improvement comprises:
  a closable opening formed within the chamber block which, when closed, defines a supernatant collection receptacle within the block; and,
  a baffle disposed within the block and adapted to deflect supernatant withdrawn through the conduit into the receptacle.

2. The chamber block of claim 1 wherein the deflection baffle comprises an inset member having a plate portion thereon, the inset member being insertable into the block such that the plate is proximal to the end of the conduit farthest from the deposition surface so that supernatant withdrawn through the conduit is deflectable by the plate portion into the receptacle.

3. The chamber block of claim 1 or 2 further comprising a closure member removably mountable to the block and adapted to close the opening therein to thereby define the enclosed supernatant collection receptacle within the block.

4. The chamber block of claim 3, wherein the closure member comprises an adhesive strip.

5. A chamber block for removable insertion into and out of a centrifuge rotor, the chamber block comprising:
  a channel through which a sample comprised of a liquid supernatant having particles suspended therein moves under the influence of centrifugal force to sediment the particles onto a deposition surface;
  a closable opening formed within the chamber block which, when closed, defines a supernatant collection receptacle within the block;
  an aperture formed in the block and communicable with the opening, the aperture also being communicable with a suction device to produce a lower pressure region in a portion of the opening;
  a conduit having a first end disposed in the vicinity of the outlet of the channel and in adjacency to the deposition surface and having a second end communicable with the portion of the opening in which a lower pressure region is produced; and,
  a deflection baffle disposed within the block and positioned with respect to the second end of the conduit such that supernatant withdrawn through the conduit toward the lower pressure region is deflectable by the baffle into the opening.

6. The chamber block of claim 5 wherein the block includes a recess communicable with the opening, and wherein the deflection baffle comprises a substantially cylindrical member sized for receipt into the recess, the member having an annular collar portion and a solid plate portion spaced therefrom, the opening through the collar portion forming the aperture, the plate portion being adapted to deflect supernatant into the opening.

7. The chamber block of claim 5 wherein the axis of the recess is substantially perpendicular to the axis of the opening.

8. The chamber block of claim 5 further comprising a seal member having an opening disposed therein, the opening in the seal communicating with the opening in the collar, the seal being adapted to form a landing to receive a connection with a suction device.

9. A centrifuge for depositing particles suspended in a supernatant onto a deposition surface comprising:
  a rotor having a region adapted to receive a deposition surface therein;
  a chamber block removably insertable into the region, the chamber block comprising: a channel through which particles and supernatant move under the influence of centrifugal force toward the deposition surface; a conduit through which supernatant is withdrawn by suction from the region of the deposition surface; a closable opening sized formed within the chamber block which, when closed, defines a supernatant collection receptacle within the block; and a baffle to deflect supernatant withdrawn through the conduit into the receptacle; and,
  means for connecting the chamber block to a suction device.

10. The centrifuge of claim 9 further comprising a closure member removably mountable to the block removably mountable to the block and adapted to close the opening therein to thereby define the enclosed supernatant collection receptacle within the block.

* * * * *